United States Patent [19]

Ritter

[11] Patent Number: 4,626,310

[45] Date of Patent: Dec. 2, 1986

[54] SURGICAL ADHESIVE SYSTEMS FOR HARD BODY TISSUES

[75] Inventor: Wolfgang Ritter, Hilden, Fed. Rep. of Germany

[73] Assignee: Henkel Kommanditgesellschaft auf Aktien, Duesseldorf, Fed. Rep. of Germany

[21] Appl. No.: 732,801

[22] Filed: May 10, 1985

Related U.S. Application Data

[63] Continuation of Ser. No. 460,901, Jan. 25, 1983, abandoned.

[30] Foreign Application Priority Data

Feb. 10, 1982 [DE] Fed. Rep. of Germany ....... 3204504
Aug. 9, 1982 [DE] Fed. Rep. of Germany ....... 3229635

[51] Int. Cl.$^4$ ................................................ C09J 5/02
[52] U.S. Cl. .................................. 156/307.3; 156/155; 156/310; 156/314; 156/332; 424/81; 433/228.1; 523/116; 523/118; 526/196; 526/318.3; 526/328; 526/329.5
[58] Field of Search ...................................... 526/318.3

[56] References Cited

U.S. PATENT DOCUMENTS

| | | | |
|---|---|---|---|
| 2,141,546 | 12/1938 | Strain ................................. | 526/317 |
| 3,221,745 | 12/1965 | Coover et al. ....................... | 156/332 |
| 3,238,186 | 3/1966 | Schultz et al. ....................... | 526/196 |
| 3,333,025 | 7/1967 | Bader .................................. | 260/880 |
| 3,725,504 | 4/1973 | Owston .......................... | 260/876 R |
| 3,829,973 | 8/1974 | Masuhara et al. .................. | 433/228 |
| 3,832,274 | 8/1974 | Owston ............................... | 161/183 |
| 3,890,407 | 6/1975 | Briggs et al. .................... | 260/878 R |
| 3,994,764 | 11/1976 | Wolinski ............................. | 156/218 |
| 4,181,983 | 1/1980 | Kulkarni ............................. | 433/228 |
| 4,243,462 | 1/1981 | Hori et al. ........................... | 156/310 |

FOREIGN PATENT DOCUMENTS

2321215 11/1973 Fed. Rep. of Germany .

OTHER PUBLICATIONS

Abstract of Japanese Pat. No. 4,214,318 published by Derwent Publications Ltd.
Abstract of Japanese Pat. No. 4,529,195 published by Derwent Publications Ltd.
G. M. Brauer, Org. Coat. Plast. Chem. 42, 321 (1980).
J. W. Prane, Org. Coat. Plast. Chem. 40, 338 (1979).
G. Giebel et al, Biomed. Techn. 26, 170 (1981), (not translated).
D. C. Miln et al, Scot. Med. I, 17, 108 (1972).
A. M. Reed et al, Polymer 24, 499 (1981).
J. M. Antonucci, Polymer Science and Technology 14, 357 (1981).
R. A. Miller et al, J. Biomed. Mat. Res. 1977, 11, 711–719.

*Primary Examiner*—John J. Gallagher
*Attorney, Agent, or Firm*—Ernest G. Szoke; Henry E. Millson, Jr.

[57] ABSTRACT

Surgical adhesive systems for the bonding of hard body tissues which contain as a polymerization initiating starter an organoboron compound and a resorbable (meth)acrylate component which is liquid to solid at room temperature and which consists of (meth)-acrylic acid esters with (meth)-acrylate groups on polyester oligomer chains from hydroxycarboxylic acids, preferably having 2 (meth)-acrylate groups in the $\alpha, \omega$ positions on the oligomer chains, and wherein the polyester oligomers are preferably formed from monohydroxymonocarboxylic acids.

25 Claims, No Drawings

SURGICAL ADHESIVE SYSTEMS FOR HARD BODY TISSUES

This application is a continuation, of application Ser. No. 460,901, filed Jan. 25, 1983, now abandoned.

BACKGROUND OF THE INVENTION

This invention relates to new self-hardening synthetic material systems that harden under the influence of oxygen from the air which are used as surgical bonding or adhesive materials to bond hard body tissues and/or for the in situ formation of synthetic parts during surgical procedures in human and veterinary medicine. A particular property of the new synthetic materials which is obtained by this invention lies in its resorbability by metabolic actions of the body where, if desired, the time period of the resorption process can be controlled.

The rapid, durable joining of separated bones or the attachment of synthetic implants in either bones or dental materials is an old dream of surgeons. Until the present, mainly polymethacrylates, epoxide resins, and polyurethane systems have been investigated. In practice, only polymethacrylates have been used successfully. They are mainly used for the implantation of joint prostheses, the cementing together of metal and bone, fusion of vertebrae, the repairing of defects in the cranium, and the implantation of support materials in facial reconstructive surgery.

In addition to these applications, it is desirable to find additional areas of application for adhesives or cement for bones, such as in connection with anatomical repositioning, fixation, and retention of bone fragments for shattered fractures or joint breaks. It is desired to obtain a permanent joining of bone fragments and to obtain immediate use after hardening of the cement or adhesive material. It would be especially desirable to have the repositioning, fixing, and retention of bone fragments made reversible with the help of resorbable adhesive component systems. The adhesives or cement for the bones should be resorbed by the body as soon as the body has formed new bony material. In addition, it is important that the stabilizing of fractures by means of plates or splints be made reversible when they are attached by means of adhesives. The use of splints or plates made of metal or synthetic materials by the use of holes drilled in the bones and the application of screws would no longer be needed. When using resorbable supporting materials; for example, those made of polylactic acid or polyglycolic acid, the second operation could be omitted.

Adhesives or cements used for such purposes must, among others, meet the following requirements: chemical stability: maintenance of physical properties, even under the influence of body fluids within the required time range: biological compatibility: no carcinogenic properties: no allergenic properties or other sensitizing properties: complete mechanical use after hardening: in situ manufacture of the synthetic material parts in the desired shape: easily sterilizable: good curing time: and very little changes in volume or the development of heat during curing. Especially in the area of resorbable synthetic materials, there are present the additional requirements of resorbability within a given time frame by metabolic processes in the body, as well as freedom from damaging secondary reactions from by-products.

The methacrylate systems used up till now consist of the following components: one or more free radical polymerizable monomers, a free radical starter system to start the polymerization, polymers to improve cohesion and adjust the viscosity, and filler materials to improve the mechanical properties.

As polymerizable monomers, in addition to methylmethacrylate in combination with methacrylic acid, a number of other systems have become of practical importance—compare herewith J. M. Antonucci, Polymer Science and Technology, 14, 357 (1981). With respect to hardening systems for use at room temperature with polymerizable methacrylate systems, a broad pallet of accelerators is available today—compare, for example, G. M. Brauer, Org. Coat. Plast. Chem. 42, 321 (1980) as well as J. W. Prane, Org. Coat. Plast. Chem. 40, 338 (1979)—although improvements would be very desirable here.

It is also known that the adhesion of methacrylate adhesives on bony materials can be improved through boronalkyl hardeners. Boronalkyl compounds such as, for example, triethyl, tripropyl and tributyl borons are capable of initiating free radical polymerizations in the presence of oxygen from the air. They are therefore suitable as hardeners for two component methacrylate adhesives. See, in this connection, Japanese Patent Application Nos. 42 14 318 and 45 29 195 as well as German Patent Application No. 23 21 215. Japanese Application No. 42 14 318 suggests the use of trialkyl borons as hardeners for adhesives in dental medicine and as filler materials. When using trialkyl borons, there is obtained strengths which have not so far been obtainable with any other hardeners. The probable reason for this is that the trialkyl borons will initiate the graft polymerization of collagen—see Shikai-tenbo 32, 609 (1968). The adhesive or filler material will attach by means of a covalent chemical bond onto the tooth structure.

However, the use of trialkyl boron compounds, such as trimethyl, triethyl, tripropyl and/or tributyl boron presents unusual safety problems and technological difficulties. For example, triethyl boron has an ignition temperature of $-20°$ C. In order to alleviate such severe disadvantages, it has been suggested that the trialkyl boron compounds be reacted with amines or with controlled amounts of oxygen—see Japanese Application No. 45 29 195 and German Application No. 23 21 215. However, the spontaneous ignition of these systems is not thereby avoided. The ignition temperature is only shifted thereby into the temperature range of $0°$ to $70°$ C. Therefore, the manufacture of larger quantities of adhesives is impossible and their use limited accordingly.

In order to improve cohesion and to adjust to a viscosity which is preferred for application purposes, and to reduce the volume contraction during hardening, it is known to add polymers to the monomers, such as polymethyl methacrylate, polychloroprene, chlorosulfonated polyethylene, nitrile rubbers and/or polyurethanes—see e.g. U.S. Pat. Nos. 3,333,025; 3,725,504; 3,832,274; 3,890,407 and 3,994,764.

To improve hardness and shape stability, it was found advantageous to add filler material in finely divided form; crystalline systems due to their higher packing density than amorphous fillers are much superior—see, in this connection, A. K. Abell, et al, Pol. Sci. and Technology 14, 347 (1981).

The monomers used in adhesive systems, as well as the starter systems used therein, influence the stability of the adhesive. When bonding hard tissues in medicine, the resulting strength is dependent on the pretreatment of the bones and on the storage conditions of the fitted parts. For the use of adhesive systems in the animal body, bond strengths on degreased and dried bony tissues have little meaning. More relevant is the bonding of non-pretreated, damp and greasy bones and the strength measurements of the samples after storage in blood-Ringer solution. Under such simulated in vivo conditions, when using conventional methacrylate adhesives and bone cements on bone materials, there are obtained strengths of about 60 Ncm$^{-2}$ (see, in this connection, G. Giebel et al, Biomed. Techn. 26, 170 (1981)). These strength values are too low for a number of areas of application, such as when joining bone fragments in order to obtain immediate usage thereof after hardening of the cement or adhesive. This results in a limitation in the application of these bone cements.

It is also known that certain synthetic materials will be decomposed by living organisms. Commercially available sutures based on polyglycolic acid or polylactic acid are resorbed by the organism. Use of these materials in dental medicine and orthopedic medicine are known. As far as the decomposition of these polymers are concerned, quantities of data are available—see, for example, R. A. Miller et al, J. Biomed. Mat. Res. 1977, 11, 711-719; D. C. Miln et al, Scot. Med. I, 17, 108 (1972) as well as A. M. Reed et al, Polymer 24, 499 (1981). By the co-condensation of glycolic acid and lactic acid, the rate of decomposition can be adjusted within a wide range—see, e.g., the above-mentioned literature citations.

Polyglycolic acid is usually obtained from glycolic acid through the intermediate step of glycolic anhydride with a suitable catalyst at a temperature in the range of 180° to 200° C. The direct polycondensation of glycolic acid at 118° C. and 5 mbar will result in oligomeric products with low cohesion—see A. M. Reed et al, above.

Polyglycolic acid and/or polylactic acid have not been used in medicine as an adhesive or cement. Adhesives and cements should be applied in liquid form which, after application, will form a solid polymer. Based on their high required reaction temperature, the in situ manufacture of polyglycolic acid and polylactic acid is not possible for the bonding of substrates in the animal body.

DESCRIPTION OF THE INVENTION

The object of the present invention is to create adhesives or self-hardening synthetic materials to be used in medicine, especially in combinations having the following properties: high cohesion and simultaneously good adhesion on damp and greasy surfaces, as well as decomposition of the hardened synthetic material in the organism, especially where the rate of decomposition can be controlled.

A further object of this invention is to obtain adhesives that can be hardened for use in surgery for human and animal medical applications, as well as adhesive systems to bond hard body tissues such as bones—and if desired to bond the bones to foreign body materials such as synthetic materials or metals. These adhesive systems that can be hardened are also usable for the in situ manufacture of individually shaped parts.

The object of this invention in accordance with a first embodiment is to make available a surgical bonding system to bond hard body tissues, which system is based on a polymerizable (meth)-acrylate adhesive and a polymerization initiating starter, wherein a resorbable (meth)-acrylate component of the system contains a (meth)-acrylic acid ester with (meth)-acrylate groups on polyester oligomer chains formed from hydroxycarboxylic acids, that are liquid to solid at room temperature, and wherein the reaction initiator for the polymerization or hardening reaction are organoboron compounds. In addition, the object of this invention includes the use of such bonding material systems to bond hard body tissues such as bones to each other or, if desired, also to foreign materials such as synthetic materials or metals.

Another object of this invention is the use of bonding material systems of the described type for in situ manufacture of individual shaped parts, especially in connection with the bonding of hard body tissues together with synthetic materials and/or metals.

Polymerizable (meth)-acrylate Components

The main component of the adhesive systems of the invention are reactive monomers based on acrylates or methacrylates referred to hereinafter as "(meth)-acrylate compounds", and wherein the corresponding methacrylate compounds are especially important. These reactive (meth)-acrylate compounds which have not previously been described are the subject of German Patent Application No. D 6529 (P 32 04 504.2). When used as adhesives they exhibit a number of very desirable properties. Due to their low vapor pressure, they have very low volatility. Despite their relatively high molecular weight, they can form liquids or at least viscous spreadable pastes at room temperature. They have good miscibility with components normally used in adhesive systems. Very strong elastic adhesive bonds can be formed from them. In particular, the reaction monomers of that invention when hardened can be resorbed by the living organism. Their application in this area of surgical work will assure the reversibility of bonding, strengthening and fastening elements and the like which, for example, will exhibit, when used in bone fractures, a time dependent activity because they are resorbed into the body.

The (meth)-acrylate derivatives used in the practice of this invention contain one or, preferably, several (meth)-acrylate groups on an oligomer polyester chain which has been formed from hydroxycarboxylic acids. Preferred are those (meth)-acrylate compounds which have two (meth)-acrylate groups on a polyester oligomer segment. Those compounds are suitable for use herein. Also, mixtures of different compound types fall within the scope of the present invention, especially those consisting of components with only one (meth)-acrylate group and those with two (meth)-acrylate groups on a polyester oligomer segment.

For practical use, the more important types are those having two (meth)-acrylate groups in the molecule wherein these functional groups are preferably situated terminally on the oligomer segment in such a manner that both terminal units ($\alpha,\omega$-positions) of the oligomer segment are each substituted with a (meth)-acrylate group.

The polyester-oligomer chain is formed from monohydroxymonocarboxylic acids, wherein the oligomer chains contain the structural characteristic

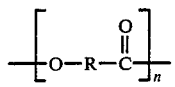

in which R is a straight or branched chain alkyl group, an unsubstituted or alkyl substituted cycloalkyl group, or an unsubstituted or alkyl substituted phenyl group, with R preferably having from 1 to 20 carbon atoms, more preferably from 2 to 10 carbon atoms, and most preferably from 2 to 7 carbon atoms; and n is an integer dependent on the selection of the R group, and is preferably chosen so that the mean molecular weight of the polyester-oligomer chain is in the range of from about 200 to about 600, more preferably about 300 to about 500.

The above polyester-oligomer chains are obtained through oligomerization of a hydroxycarboxylic acid, or a mixture of hydroxycarboxylic acids, of the formula

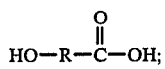

wherein R has the meaning given above. For the formation of polyester-oligomers certain selected individual hydroxycarboxylic acids or a mixture of several hydroxycarboxylic acids can be used. Especially important hydroxycarboxylic acids for the formation of these intermediates of the new (meth)-acrylate compounds are glycolic acid, the isomers of lactic acids, the isomers of α- or β-hydroxypropionic acids, the isomers of α-,β- or γ-hydroxybutyric acids, o-hydroxybenzoic acid (salicylic acid), m-hydroxybenzoic acid and/or p-hydroxybenzoic acid. Certain isomers of the listed acids as well as mixtures thereof can be used.

The polyester-oligomers are best prepared by the use of monofunctional and/or preferably by the use of difunctional coreactants, which fulfill a many faceted function. On the one hand, when using these reactants, control of the mean molecular weight of the polyester-oligomers and adjustment of the desired viscosity range is achieved. On the other hand through the selection of the functional groups of the coreactants used it is possible to form on the polyester-oligomers uniform terminal hydroxyl groups or terminal carboxyl groups, which is normally not the case with polymers or oligomers of a hydroxycarboxylic acid. Finally by using selected monofunctional coreactants, it is possible to eliminate one reactive terminal group of the polyester-oligomer, so that for this type of compound only one reactive function is available for the subsequent attachment of the (meth)-acrylate group. By suitable admixture of monofunctional and difunctional coreactants it is possible to obtain predetermined mixture ratios of mono-(meth)-acrylate compounds and bis-(meth)-acrylate compounds.

As monofunctional coreactants, especially suitable are monoalcohols, monocarboxylic acids and/or monoamines, i.e., primary, secondary and/or tertiary monoamines. Difunctional coreactants for the preparation of the polyester-oligomers are difunctional alcohols or dicarboxylic acids, or functionally reactive dicarboxylic acid derivatives, especially the corresponding anhydrides, esters, halides, and the like.

If oligomers as hereinabove described are prepared through cocondensation of hydroxycarboxylic acids and diols, there are obtained polyester-oligomers with terminal hydroxyl groups. The quantity of diols used, together with the reaction conditions, determine the mean molecular weight of the resulting polyester-oligomers. Polyester-oligomers having terminal hydroxyl groups can be easily transformed by reacting them with acid anhydrides to form analogous derivatives having terminal carboxyl groups.

On the other hand, if the oligomers are obtained through cocondensation of hydroxycarboxylic acids with dicarboxylic acids or reactive dicarboxylic acid derivatives, there is obtained directly polyester-oligomers with terminal carboxyl groups or derivatives of carboxyl groups. The coreactant which is used acts as a control, standardizes the terminal reactive groups, and regulates the molecular weight. Information known in the art for the manufacture of polyesters or copolyesters is also applicable here. The use of monoalcohols and/or monoamines will cause the desired blocking of the terminal carboxylic acid groups in the polyesteroligomers, while the use of monocarboxylic acids blocks the terminal hydroxyl group positions on the oligomers.

In all instances described herein, modified polyesteroligomers are formed which can be easily converted by known methods to (meth)-acrylate compounds. For example, if there are terminal hydroxyl groups on the polyester-oligomers, the (meth)-acrylic acid group is introduced through esterification or transesterification or by a comparable reaction with acrylic acids or acrylic acid esters and/or especially the corresponding methacrylic acid compounds. Also, if there are terminal carboxyl groups in the polyester-oligomers, the desired (meth)-acrylate groups can readily be attached by known methods. Suitable here, for example, is the reaction of the oligomer intermediate product with glycidyl esters of acrylic acid or methacrylic acid. By splitting of the glycidyl group, the (meth)-acrylate group is attached via the glyceride group to the monocarboxylic or dicarboxylic acid formed as the intermediate.

In general, the selection of the monofunctional or difunctional coreactants, which are used herein in only minor amounts, can be made practically without limitations. These reactants can be based on saturated or olefinically unsaturated aliphatic or cycloaliphatic groups or they can be aromatic in nature, e.g. phenyl or alkyl substituted phenyl. Generally, they do not contain more than 25 carbon atoms, and preferably not over 15. Suitable diols contain, for example, 2 to 20 carbon atoms, preferably 2 to 10, and more preferably 2 to 6 carbon atoms in the molecule. The same limitations also apply for the corresponding dicarboxylic acids. Examples of suitable diols include ethylene glycol, diethylene glycol, triethylene glycol, tetraethylene glycol, propylene glycol, dipropylene glycol, 1,3-butylene glycol, 1,4-butylene glycol, 2,2-dimethyl-1,3-propanediol, 2,2,4-trimethyl-1,6-hexanediol, 1,3-cyclohexanedimethanol, 1,5-pentanediol, 1,6-hexanediol, 1,10-decanediol, and 2,2-bis-(3-hydroxycyclohexyl)-propane.

To transform oligoester diols into oligoester dicarboxylic acids, the following anhydrides are quite suitable: succinic acid anhydride, glutaric acid anhydride, phthalic acid anhydride, itaconic acid anhydride, citraconic acid anhydride, as well as alkenylsuccinic acid anhydrides.

Suitable dicarboxylic acids are, for example, oxalic acid, malonic acid, succinic acid, glutaric acid, adipic acid, pimelic acid, suberic acid, azelaic acid, sebacic acid, isosebacic acid, nonanedicarboxylic acid, decanedicarboxylic acid, undecanedicarboxylic acid, dodecanedicarboxylic acid, phthalic acid, hexahydrophthalic acid, isophthalic acid, terephthalic acid and biphenyldicarboxylic acid.

As monovalent coreactants there can be used aliphatic, cycloaliphatic or aromatic monoalcohols, the corresponding monocarboxylic acids, and the corresponding primary, secondary or tertiary amines. Their carbon number can be within the ranges given above.

It is understood that in all cases, i.e., for the hydroxycarboxylic acids as well as the coreactants, not only the free reactive components of the type given above can be used, but also such reactive derivatives can be used which form by known methods under conditions of esterification or transesterification the desired polyester-oligomers of a predetermined molecular weight. Also suitable are, for example, the esters of hydroxycarboxylic acids as well as lactones or lactams of hydroxycarboxylic acids which, when reacted with diols or diol esters, can be transesterified. The manufacture of the polyester-oligomers as well as their conversion to the (meth)-acrylate compounds is carried out by known methods, for example, by reaction in the presence or in the absence of solvents, and if desired in the presence of catalysts, especially esterification catalysts.

Should mixtures of difunctional and monofunctional (meth)-acrylate compounds be chosen for use, then in a preferred embodiment, the quantity of monofunctional component is not in excess of 95 mole percent based on the mixture of monofunctional and difunctional components. More preferred are mixtures of the described type in which the content of monofunctional components is not over 50 mole percent and especially not over 10 mole percent.

In a preferred embodiment of the invention, the new (meth)-acrylate compounds are flowable or, at least, paste-like and spreadable at room temperature, and therefore they can be used as the main component or even as the sole polymerizable adhesive component in the surgical adhesives. It is thereby preferred that the liquid (meth)-acrylate compounds of the invention have a viscosity at room temperature; in the range of from about 500 to 70,000 mPas, preferably in the range of about 3000 to 50,000 mPas. Solid (meth)-acrylate compounds of the invention are readily soluble in liquid polymerizable components, such as methyl methacrylate so that such solid compounds of the invention in admixture with liquid conventional monomer constituents are converted in a simple manner to the technically desirable liquid adhesive components.

Organoboron Compounds as the Initiator Component

As the initiator component for the polymerization and curing of the adhesive systems, organoboron compounds can be used; which is the subject of a number of prior patent applications of the applicant. These initiators are all based on reactive boron components: they have the same reactivity as the known lower boron alkyls; however, they all show a definite decreased tendency for spontaneous ignition. This makes it possible to handle them easily and without danger. The organoboron compounds of the invention to be used herein show only a slow loss in activity when used in the presence of air. They can be used as separate hardener components in two component adhesive systems; it is also possible to use them as primers in systems of the so-called no-mix adhesives. The boron-containing hardeners used in the practice of the invention will guarantee high strength of the adhesive bond or of the in situ formed synthetic components. The rate of hardening can be controlled and therefore adjusted to the desired conditions of use. The structure of the initiator component guarantees good adhesion of the adhesives for bonding materials onto body materials. The hardeners of the invention to be used herein, based on organoboron compounds, are also described in the laid open European Patent Applications Nos. 81109074.5 (D 6144 EP) and 81109073.7 (D 6246 EP).

Especially important are the organoboron compounds and systems which are described in prior German Patent Applications Nos. D 6391 (P 31 43 945.4), D 6460 (P 32 01 780.4), D 6461 (P 32 01 731.6), D 6517 (P 32 07 264.3), and D 6548 (P 32 07 263.5).

Suitable initiators for the new systems can therefore be selected from the following groups of boron compounds:

(a) Boron alkyls with sterically hindered alkyl groups of the general formula

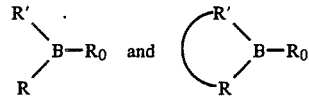

wherein R' and R are aliphatic monocyclic or dicyclic groups with 3 to 25 carbon atoms, and $R_o$ is hydrogen or a hydrocarbon group, preferably cyclic, having from 1 to 15 carbon atoms;

(b) boron compounds which are the reaction products of dihydroxy aromatic compounds with $BH_3$ or its alkylated products, having the general formula

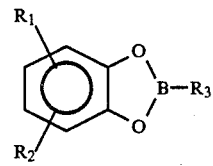

wherein $R_1$, $R_2$ and $R_3$ are either hydrogen or an alkyl group having 1 to 4 carbon atoms, and $R_1$ and $R_2$ can also be an aromatic and/or an aliphatic cyclic group;

(c) boron compounds of the general formula

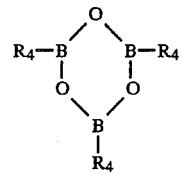

wherein $R_4$ is an alkyl group having 1 to 6 carbon atoms.

As boron alkyl compounds, there can be used a number of known boron alkyls which can be manufactured according to known methods. Typical representatives of such boron compounds are, for example, 9-borabicyclo[3.3.1]nonane, diisopinocampheyl borane, dicyclohexylborane, thexylborane(2, 3-dimethyl-2-butylborane), 3,5-dimethylborinane, and diisoamylborane. From these compounds the first named 9-borabicyclo[3.3.1]nonane is preferred for practical reasons.

A compilation of possible methods for the preparation of these boron compounds can be found in the monograph by Herbert C. Brown, 1975 "Organic Synthesis via Boranes", Publisher John Wiley & Sons. As initiators there can be used hydroborated products of dialkylboranes and olefins. As olefins, there can be used butene, isobutene, hexene, cyclohexene, vinyl chloride, allyl chloride, allyl amine, methacrylic acid methyl ester, vinyl acetate, or crotonic acid methyl ester. Among the compounds suitable for use herein should be mentioned for example: diisopinocampheylbutyl boron, thexylcyclohexylcyclopentyl boron, thexyllimonyl boron, trinorbornyl boron, B-butyl-9-borabicyclo[3.3.1]nonane, B-isobutyl-9-borabicyclo[3.3.1]nonane, B-[2-(4-cyclohexenyl)-ethyl]-9-borabicyclo[3.3.1]nonane, B-cyclopropyl-9-borabicyclo[3.3.1]nonane, B-p-tolyl-9-borabicyclo[3.3.1]nonane, and B-tert.butyl-3,5-dimethyl borinane. Additional products that are suitable for use herein are the reaction product of 1,2-dihydroxybenzene (pyrocatechol) with boron hydride (catechol borane), and tri-n-butylboroxin.

Additional especially preferred initiators or hardeners are described under (d) below:

(d) These starter systems of the invention consist of a homogeneous mixture of at least one organoboron compound which is activated by air, and an organic oligomer or polymer which is liquid to solid at room temperature and which is inert to the organoboron compound. The designation "homogeneous mixture" is understood to include single phase mixtures which are single phase at storage temperatures and use temperatures, which are characteristic of true solutions.

As organoboron compounds, there are suitable, first of all, boron alkyl and/or boron aryl compounds or the corresponding organoboron hydride compounds. Boron alkyl compounds or boron alkyl hydrides are an especially preferred class of materials. Preferred embodiments include compounds of the type:

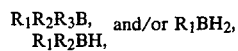

$$R_1R_2R_3B, \text{ and/or } R_1BH_2,$$
$$R_1R_2BH,$$

wherein in these general formulas, the groups $R_1$, $R_2$ and $R_3$ are hydrocarbon groups, especially alkyl groups which can also include heteroatoms, especially O, N and/or S. If at least two such inorganic groups are attached to the boron atom, they can form a ring system of their own. The borons substituted with hydrocarbon groups, in their preferred embodiment, do not contain more than about 30 carbon atoms, preferably not more than about 25 carbon atoms. It is more preferred that each organic radical on the boron does not contain more than about 15 carbon atoms.

As boron-containing initiator components, or for the preparation of suitable boron-containing initiator components, organoboron monohydride compounds, preferably the dialkylboron monohydrides, are particularly suitable for use.

A typical example of such boron compounds is, for example, 9-borabicyclo[3.3.1]nonane (9-BBN), which is listed under (a) above and is preferred for practical reasons.

As boron initiators in this embodiment, there can also be used simple trialkylboranes such as hydroborated products of mono- or especially dialkyl boranes and olefins such as are described above.

As solvents with very low vapor pressures, there can be used oligomers or polymers which are inert toward the organoboron compounds. There are no restrictions with respect to the structure thereof provided that there is a homogeneous miscibility between those used as solvents and the organoboron compounds. Suitable, therefore, are all polymers, polycondensates and/or polyaddition products which fulfill the above requirements. The average molecular weight of these oligomers or polymers as solvents lie in the range of 200 to 50,000,000 grams/mole. Depending on structure and molecular weight, these solvents can have low viscosity and be flowable to solid at room temperatures. It is desirable that the mixtures of materials containing organoboron compounds be viscous, flowable, or spreadable at room temperature. However, this is not a prerequisite for the effectiveness of the starter systems used as initiators in accordance with this invention. On the contrary, the storage stability of the mixtures of materials which are solid at room temperature are particularly good.

Suitable polymer solvents for use in this connection are, for example, polyethers, polyesters, polyamides, polyurethanes, polysiloxanes and the like. For the manufacture of flowable systems, there can be used oligomers that are liquid at room temperature having viscosities in the range of 1000 to 70,000 mPa's (room temperature) and these are especially interesting. The polyesters and the polyamides especially can be used in many ways in the practice of the invention. They can, as well as the other polymeric solvents, be manufactured according to known methods and, in this case, for example, through polycondensation of dicarboxylic acids with diols or diamines and, if desired or required, with the application of monofunctional reactants to modify or regulate the mean molecular weight. Preferred herein, as a rule, are saturated dicarboxylic acids and saturated glycols having up to 15 carbon atoms, preferably up to 10 carbon atoms in the molecule. In an analogous fashion, the above also applies to amines or diamines for the manufacture of polyamides. Suitable polyethers are, for example, polyethylene oxides or polypropylene oxides having a molecular weight in the required range. In this connection, a good knowledge of polymer chemistry is desirable.

For the preparation of starter systems, the organoboron compounds are dissolved in the inert organic oligomers or polymers with complete exclusion of oxygen. If necessary, slight heat can be applied. It is, for example, possible in order to accelerate the dissolution to heat the mixture to a temperature up to 100° C., preferably about 70° C.

When using oligomers or polymers that are solid at room temperature, the use of inert liquid solvents is suggested. Suitable are known solvents for organoboron compounds such as tetrahydrofuran or polyethers such as diethylene glycol dimethyl ether, or esters, halogenated hydrocarbons, and the like. When using these liquid adjuvants, after a homogeneous mixture is obtained the adjuvants are evacuated off, and the boron alkyl/oligomer mixture isolated. This mixture should be stored in closed vessels, preferably under an inert gas such as under nitrogen.

The content of organoboron compounds in such starter systems is usually not over about 70% by weight and, preferably, not over about 50% by weight based on the total weight of the mixture. It is also preferred that the content of organoboron compounds is at least about 1 wt. % of the total weight of the system, so that quantities of about 1 to 50 wt. %, especially 3 to 50 wt. % are particularly suitable. Another important class of compounds for practical application involves the use of polymeric organoboron compounds as initiator components which are stabilized against exposure to air. These compounds are described under (e) below:

(e) the characteristics of this class of organoboron hardeners are that polymeric organoboron compounds are used which have as substituents on a polymer matrix, borane and/or organoboron groups stabilized against exposure to air.

These boron-containing groups are preferably attached through B—C bonds to the polymer matrix. So long as the boron-containing groups are not the boryl group ($-BH_2$) itself, the boron-containing substituents in the polymer matrix in a further preferred embodiment have attached to the boron, with at least one additional B—C bond, one or two organic radicals. The preferred groups are hydrocarbon groups which can also contain heteroatoms, especially O, N and/or S. Suitable substituents on the boron are, in particular, alkyl, cycloalkyl and/or aryl groups which can be on one or both of the free valences of the boron which are not attached to the polymer matrix. When such organic groups other than hydrogen are in both boron valences, then they can together form a ring system.

When compared to the usual boron alkyl hardeners, the oligomeric and polymeric boron compounds exhibit definite advantages. They are not self-igniting and have little requirements during storage. The activity of such hardeners remains even after long storage in air. The compatibility of the polymerizable components with the hardener can be assured by suitable selection of the polymer matrix in each instance. As a rule, for the hardening of the monomer components, the quantity of oligomeric or polymeric organoboron compounds required is very small.

These polymeric boron compounds can be obtained in a simple manner in that oligomers or polymers which contain addition receptive carbon double bonds undergo hydroboration, and consequently the boron-containing groups are introduced into at least a portion of the addition-receptive double bonds. Suitable for hydroboration are diborane as well as mono- or di-substituted boranes, that is, compounds of the general formula $R_4R_5BH$, wherein in this formula $R_4$ is an organic group, preferably a hydrocarbon group, and $R_5$ is a hydrogen or an organic group which can be the same as $R_4$ or different from $R_4$, or, together with $R_4$ and the boron, can form a ring system.

The polymer matrix containing ethylenic double bonds, which are available for hydroboration, can be from low viscosity and flowable to solid, depending on their structure and molecular weight. Their mean molecular weight can have values of several million and is usually in the range of about 150 to about 3 million. Lower values within this range are normally preferred, especially those in the range of about 300 to about 500,000, and more especially in the range of about 500 to about 10,000. Also here it is desirable that the polymer matrix, and also the polymeric organoboron compounds obtained from them, be viscous to flowable or spreadable at room temperature. Here, for example, molecular weights of the polymer matrix in the range of about 300 to about 3,000 are especially suitable. For the effectiveness of the polymeric organoboron compounds used in the practice of the invention as initiators, this is not however a prerequisite. On the contrary, the storage stability of the polymeric organoboron compounds which are solid at room temperature are especially good.

The polymeric matrix prior to hydroboration can be ethylenically unsaturated to any degree. Preferred are matrix materials which prior to hydroboration have an iodine number in the range of about 1 to about 500, preferably about 5 to about 100, and more preferably about 8 to about 50.

Ethylenic double bonds available for hydroboration in the starting polymers can be in the main chain and/or in the side chain substituents.

The polymer matrix can have either a linear or branched structure, although polymeric materials with cross-linked structures are also possible for use herein.

As a polymeric matrix, all polymeric types are suitable so long as they contain double bonds which are available for hydroboration and contain no reactive groups which would lead to undersirable secondary reactions when the boron-containing groups are introduced into the polymeric material.

The polymeric material can also be obtained through polymerization or copolymerization of olefinically unsaturated components by polycondensation or by polyaddition reactions. Through suitable selection of polymers from synthesizable monomer types the desired amount of reactive double bonds for the subsequent hydroboration in the polymeric material is assured. Especially suitable as the polymer matrix are unsaturated oligomers or polymers which are obtained through a polycondensation reaction. Usable here are all the known polycondensate types such as polyesters, polyamides, polyimides, polycarbonates, polyurethanes and the like. Also suitable are oligomers or polymer types which have been obtained through polyaddition reactions. Details of the formation thereof can be found in earlier German Patent Application No. D 6461 (P 32 01 731.6).

The extent of hydroboration in the polymer matrix is limited only by the number of double bonds present. It has been found to be advantageous to have at least a substantial portion of these double bonds converted through the introduction of boron-containing substituents. In a preferred embodiment of this invention at least 30%, and preferably at least 50% of the originally present ethylenic double bonds are hydroborated in the polymer matrix. Especially suitable are such polymeric organoboron compounds wherein at least 80%, and preferably at least 90% or even at least 95% of the ethylenic double bonds have been reacted with the boron-containing component. A practically completely hydroborated material is in most cases the preferred initiator with respect to the practice of the invention.

For hydroboration there can be used, in addition to diborane ($B_2H_4$), organoboron compounds with one or two organic groups, in particular, hydrocarbon groups. The preferred organic groups are alkyl, cycloalkyl, and/or aryl groups where two of the available groups together with the inclusion of the boron atom can form a ring. The substituted hydrocarbon groups preferably do not contain more than 25 carbon atoms, more preferably not more than about 15 carbon atoms.

An especially suitable class of organoboron compounds for the preparation of the polymeric initiator components are organoboronmonohydride compounds, especially dialkymonohydrides. A typical representative of such boron compounds is here also 9-borabicyclo[3.3.1]nonane, which is preferred for practical reasons.

A further interesting class of organoboron initiators are described as follows under f):

(f) In this embodiment the substituted organoboron compounds are characterized in that the boron-hydride group or organoboron group contains a fatty acid ester and/or a fatty alcohol ester.

These boronalkyl compounds are hydroborated adducts of diborane and/or organoboron compounds with at least one B—H bond on fatty acid esters and/or fatty alcohol esters wherein at least one portion of the fatty acid group and/or fatty alcohol group contains carbon-carbon double bonds receptive to addition reactions.

Concerning the composition and preparation of this class of boronalkyl compounds, the following is applicable:

Esters or ester mixtures which serve as the matrix contain on B—C bonds as substituents boronhydride groups and/or organoboron groups. To the extent these boron-containing groups do not represent the boryl group (—BH$_2$) itself, such boron-containing substituents in a preferred embodiment have attached to the boron with at least one additional B—C bond one or two organic groups. Preferred groups are hydrocarbon groups, which can optionally contain heteroatoms, especially O, N, and/or S. Suitable substituents on the boron are preferably alkyl, cycloalkyl, and/or aryl groups, which are in one or both valences of the boron which are not attached to the ester matrix. In the event the organic groups other than hydrogen are on both boron valences, they can together form a ring system.

These boron compounds can be produced in a simple manner, when the starting material containing the ester matrix having olefinic double bonds has been subjected to hydroboration with diborane, or preferably with monosubstituted and especially with disubstituted boranes of the general formula $R_6R_7BH$, wherein in this formula $R_6$ is an organic group, preferably a hydrocarbon group, and $R_7$ is hydrogen or also an organic group, which can be the same as $R_6$ or different from $R_6$ or together with $R_6$ can form a ring system with the boron. Preferred organic groups are alkyl, cycloalkyl and/or aryl groups. The hydrocarbon groups which substitute the boron preferably contain not more than 25 carbon atoms, preferably not more than 15 carbon atoms. In an especially preferred embodiment, $R_6$ and $R_7$ together with the boron atom forms a ring system which does not exceed the above values for the number of carbon atoms. Here also the above mentioned 9-BBN is preferred for practical reasons.

Of decisive importance is the ester base that serves as the matrix. The starting materials for this matrix are characterized in that they are monofunctional fatty acids and/or monofunctional fatty alcohols which are converted into esters or ester mixtures, wherein at least one portion of their fatty acid and/or fatty alcohol components have a carbon-carbon double bond receptive to addition reactions.

The terms fatty acids and fatty alcohols encompass monofunctional components of the named type with a carbon atom number in the range of about 8 to 32 carbon atoms, preferably in the range of about 14 to 22 carbon atoms. The unsaturated fatty acids or unsaturated fatty alcohols can be of synthetic or natural origin. Preferably there are used singly or multiply olefinically unsaturated alkene monocarboxylic acids or monoalkenols of the required carbon number. The carbon chains of these fatty acids or fatty alcohols can be straight chain and/or branched.

The complementary components forming the esters can be either a monohydroxy or polyhydroxy alcohol or, respectively, a monofunctional or a polyfunctional carboxylic acid. It is possible to have the addition available carbon-carbon double bonds in only one constituent, i.e., only in the fatty acid or the fatty alcohol; however, both ester forming components can contain olefinic double bonds. For the preparation of the boron alkyl compounds used in the practice of the invention, at least a substantial portion of these double bonds will be subjected to hydroboration.

In a preferred embodiment, the ester matrix is formed through esterification of a monofunctional component (acid or alcohol) with a polyfunctional complementary component (alcohol or acid).

Especially preferred matrix materials are esters of unsaturated monocarboxylic acids (unsaturated fatty acids) with polyhydroxy alcohols. As the polyhydroxy ester-forming reaction component, especially suitable are those compounds which have a functionality up to 6, preferably with a functionality of 2 to 4. In this preferred embodiment for the matrix for the boron-containing substituents, monocarboxylic acids of the stated carbon number range are esterified with polyhydroxy alcohols, in particular with dihydroxy alcohols, trihydroxy alcohols, or tetrahydroxy alcohols.

It is advantageous to have the polyfunctional ester components with a relatively low number of carbon atoms which, for example, can be in the range of 2 to 10, preferably in the range of 2 to 6 carbon atoms. As polyfunctional alcohols, especially suitable are the lower glycols such as ethylene glycol, propylene glycol-1,2, propylene glycol-1,3, the $C_4$ glycols with terminal and/or internal hydroxyl groups, or the corresponding $C_5$ and $C_6$ compounds. An especially preferred alcohol for use herein is glycerine or polyhydroxy alcohols of the pentaerythrite type. On the other hand, monofunctional fatty alcohols can be esterified with lower polycarboxylic acids, in particular, with lower dicarboxylic acids or lower tricarboxylic acids.

It is also possible to use synthetic or natural fats and/or oils as the ester matrix for the subsequent hydroboration. Unsaturated esters in admixture with saturated components such as mixtures with saturated esters and/or in mixtures with different unsaturated esters can be used.

Esters of corresponding fats and/or oils which contain ethylenic double bonds available for hydroboration can be either low viscosity and flowable to solid depending on their structure and molecular weight.

The unsaturated esters or ester mixtures such as fats, oils and the like can be ethylenically unsaturated in various degrees prior to hydroboration. Preferred as suitable starting materials are those having an iodine number of up to about 280, preferably in the range of about 1 to about 205. Within this range the value of the iodine number of from about 5 to about 130 is especially preferred.

The extent of hydroboration of the ester matrix can be selected freely within the framework of the total number of available double bonds. It has been proved advantageous when at least a substantial portion of these double bonds are converted by the introduction of the boron-containing substituents. In a preferred embodiment, more than 30%, preferably at least 50%, and more preferably at least 70% of the ethylenic double bonds of those originally available in the ester matrix are hydroborated. Especially preferred are those organoboron compounds in which, in relation to the reaction starting materials, at least 80%, preferably at least 90%, or even at least 95% of the ethylenic double bonds contain the boron-containing constituents.

For hydroboration, the unsaturated esters are reacted with the selected boronhydride compounds under complete exclusion of oxygen. It is advantageous here to work in the presence of solvents. Suitable are the known solvents for organoboron compounds, especially tetrahydrofuran, glycol, polyethers such as diethyleneglycol-dimethylether, esters, hydrogen halides, and the like. The reaction is preferably carried out in a temperature range of about 0 to about 100° C., preferably in the range of about room temperature to about 70° C.

Additional Particulars of the Invention

The bonding systems of the invention, consisting of polymerizable component A and hardener or initiator component B, can be made into a two component formulation. For practical purposes the adhesive component A can be mixed with hardener component B prior to application to the parts to be bonded together. The open time of the adhesive can be adjusted by selecting the amounts of component A and B to meet this requirement.

Formulating of the adhesive systems of the invention is also possible when following the "No-Mix Adhesives" or "Acrylate Adhesives of the second or third generation" (compare "Adhesives Age", 1976, 21–24 as well as "Adhaesion", 1981, 156–161). For these types the separate mixing of the adhesive component and the hardener component can be omitted. Initially, the initiator component is applied in a thin layer to one or both of the surfaces to be glued together and then the adhesive component is applied. The bonding is achieved by fixing the parts in the desired position.

The above enumerated organoboron compounds under (a) through (f) can be used as the primer phase or can be used in the primer phase. In this connection, of special importance are the organoboron systems listed under (d) through (f). In particular, a hardener system is important in this connection which is disclosed in earlier German Patent Application No. D 6391 (P 31 43 945.4) (correspondong U.S patent application Ser. No. 438,412, filed Nov. 1, 1982), and which can be manufactured as follows:

(g) In a first process step, the polymerizable monomers containing ethylenic double bonds are polymerized through the addition of organoboron compounds under the exclusion of oxygen. After obtaining a concentration required for processing, this polymerization is discontinued through the addition of an anionic inhibitor.

Advantage is taken of the fact known throughout the literature that organoboron compounds react not only under a free radical mechanism with the addition of oxygen, but also in the absence of oxygen the ethylenically unsaturated monomers can be polymerized by means of organoboron compounds in a slowly occurring anionic mechanism. This relatively slow reaction process will cause a thickening of the initially slightly fluid monomer phase under the influence of the organoboron compounds. As soon as sufficient thickening is obtained through polymerization, the anionic polymerization is terminated. In this instance also, hardener component B consists of a mixture of organoboron components and polymeric components.

As the ethylenically unsaturated monomers, derivatives of acrylic acid and/or methacrylic acid are especially suitable; in particular, the corresponding esters with monofunctional or polyfunctional alcohols as well as the corresponding acid amides which can be substituted on the amide nitrogen, for example, with hydrocarbon groups according to known methods.

As inhibitors or stabilizing agents for anionic polymerization all those compounds are suitable which are used for stabilizing α-cyanoacrylic acid ester components, such as phosphoric acid, boric acid, boric acid esters and the like, sulfonic acids, or sultones. Especially suitable inhibitors are carboxylic acids with free carboxyl groups. It is advantageous to use olefinically unsaturated carboxylic acids, which, due to their double bonds, react on one hand with the organoboronhydride compounds, and on the other hand through their double bonds in a polymerization reaction, thereby becoming an active adhesive constituent. Especially suitable acid inhibitors against anionic polymerization are acrylic acids and/or methacrylic acids. The free carboxyl groups thereof not only terminate the anionic polymerization process, but the adhesive systems have improved bonding properties in a known manner due to the free carboxylic acid groups.

Finally, in accordance with this invention, it is also possible to use single component adhesive systems that are based on information given in European Patent Application No. 0 051 796 (D 6246 EP) with respect to the polymerizable component which contains the above mentioned resorbable (meth)-acrylate compounds.

(a) Ratio of Hardener to Adhesive Components

In order to harden the reaction systems of the invention there is used about 0.1 to 40 wt. % of the desscribed polymeric boron initiators, especially about 0.1 to about 30 wt. %, in relation to the weight of the polymerizable constituent. Preferred is the use of the polymer hardeners in a quantity of about 0.5 to about 30 wt. % based on the polymerizable constituent.

(b) Additional Polymers that can be Used

Quite often the polymerizable components, in addition to containing the polymerizable substances, can contain premanufactured polymers such as polymethyl(meth)-acrylate, copolymers of methyl(meth)acrylate, polychloroprene, chlorosulfonated polyethylenes, nitrile rubbers, and urethanes for strengthening and adding resilience as well as acting as thickening agents. In order to guarantee that the hardener system will depolymerize in use, polyhydroxycarboxylic acids such as polyglycolic acid and polylactic acid are especially suitable. This makes the processing of the material, for example the adhesive, simpler. In particular, this makes current technology applicable hereto.

In many instances it is required or desired to use further auxiliary materials such as fillers, e.g. quartz powder or the like. Finally, it may be advantageous to use suitable coloring agents or pigments.

(c) Co-monomers Which can also be Used Herein

As additional polymerizable constituents there can be used in the synthetic materials of the invention the numerous known compounds with polymerizable ethylenic double bonds which are normally used in, for example, casting resins, fillers, and in particular in reaction adhesives. Especially suitable are the esters of acrylic acid and/or α-substituted acrylic acids, such as methacrylic acid, which are referred to hereinafter as "(meth)-acrylic acid compounds", with monohydroxy or polyhydroxy, especially dihydroxy, alcohols. Also suitable are other known derivatives of (meth)-acrylic acid, in particular the corresponding acid amides which can be substituted on the amide nitrogen, for example, with hydrocarbon groups. Other possible substituents in the α-position of the (meth)-acrylic acid compounds are for example halogen, especially chlorine and/or bromine, cyanide, or the usual alkyl groups having up to 10 carbon atoms.

As examples of the (meth)-acrylic acid esters of monohydroxy alcohols are: (meth)-acrylic acid methylester, (meth)-acrylic acid ethylester, (meth)-acrylic acid butylester, (meth)-acrylic acid ethylhexylester.

Examples of the corresponding esters with polyhydroxy alcohols are those with ethyleneglycol, diethyleneglycol, polyethyleneglycol, and trimethylolpropane, di- and mono-(meth)-acrylic acid esters of glycerine, di-(meth)-acrylic acid esters of tri- and tetraethyleneglycol, of di-, tri-, tetra- and pentapropyleneglycol, and the di-(meth)-acrylic acid esters of ethoxylated or propoxylated diphenylolpropane. (Meth)-acrylic acid esters of alcohols can also be used which are derivatives of dihydroxymethyltricyclodecane or those based on tricyclodecane in which two alcohol functions in the ring system are elongated when reacted with dicarboxylic acids such as maleic acid or cyclohexanedicarboxylic acid or terephthalic acid.

Reaction products of diglycidylethers of diphenylolpropane with methacrylic acid and/or acrylic acid can also be used. Reaction products of diisocyanates or triisocyanates, for example toluylenediisocyanate, diphenylmethanediisocyanate, isophoronediisocyanate, trimerized toluyleneisocyanate and the like with hydroxyalkyl-(meth)-acrylates can be used as a polymerizable component.

Suitable are also polymerizable monomers such as vinyl acetate, vinyl halides, for example vinyl chloride, vinyl bromide, or vinyl fluoride, styrene, diphenylbenzene, crotonic acid esters, and maleic acid esters or the so-called styrenized unsaturated polyester resins. These compounds are usually present in only minor amounts in the reaction adhesives, for example, in quantities up to about 25 wt. % of the polymerizable components.

In addition there can also be used 2-acryloyloxyethylphosphate, 2-methacryloyloxyethylphosphate, bis-2-acryloyloxyethylphosphate, bis-2-methacryloyloxyethylphosphate, tris-2-acryloyloxyethylphosphate, tris-2-methacryloyloxyethylphosphate, and acid amides such as dimethylene-bis(meth)-acrylamide, tetramethylenebis(meth)-acrylamide, trimethylhexamethylenebis(meth)-acrylamide, tri(meth)-acryloyldiethylenetriamine, and the like.

EXAMPLES

Test Samples (See G. Giebel et al., Biomed, Techn. 26, 170 (1981).

Test samples of cattle bones having the measurements 50×20×5 mm are cut in the middle at an exact right angle to the side areas (50×5 mm) using a diamond cutting saw with water cooling.

In this manner accurately fitting parts with a contact area of 1 cm² are obtained.

Pretreatment of the Test Samples (See Giebel et al., above)

The bony test materials, which were not treated any further, were then placed for two hours into a warm Ringer solution at 37° C. in order to thoroughly wet the bones.

Sealing (a) 2-K-adhesives

Adhesive resin (A) and hardener (B) are mixed together. The mixture is then applied to damp bones.

(b) No-Mix Adhesives

Only the hardener (A) is applied in a thin layer on both of the surfaces to be joined together. Following this the adhesive resin (B) is applied. The test specimens are joined together in a press made of PVC and then 5 N pressure is applied. The adhesive press prevents side-to-side movement of the test specimens during curing.

Curing Conditions (See Giebel et al., above)

The joined bones are left for 20 minutes in the adhesive press in an environmental chamber at 37° C. and about 100% relative humidity. Following this they are removed from the adhesive press and stored for 20 hours in Ringer solution at 37° C.

Strength Measurement

The tensile strength of the joined bones is measured using a Universal test device which pulls them apart at a velocity rate of 12 mm/min.

Due to the broad range of measured values for these natural substrates, the range of strengths listed are based on 6 individual experiments.

RESIN COMPONENT A

Example 1–6

Oligohydroxycarboxylic Acids with Hydroxyl End Groups (a) Obtained from glycolic acid and ethylene glycol Into a three-necked flask equipped with stirrer and reflux condenser, glycolic acid and ethylene glycol are introduced. Under nitrogen, rapid heating is carried out to 150° C. and then during the course of 6 hours from 150° to 200° C. Most of the reaction water separates which indicates the reaction of the ester condensation. The make-up is then cooled to 150° C., carefully evacuated at 10 Torr, and the reaction is completed at 200° C. and 10 Torr. After 30 minutes the product is decanted hot at 150° C. The composition of the make-up and the oligomeric properties are given in Table 1 (Examples 1–3).

TABLE 1

| Oligohydroxycarboxylic acids with hydroxyl end groups from glycolic acid and ethylene glycol | | | | | | |
|---|---|---|---|---|---|---|
| | Adducts | | Reaction water, | | Calculated molecular | |
| Example | glycolic acid mole | ethylene glycol mole | % of theory | Acid Number | weight g/mole | Appearance |
| 1 | 3 | 1 | 100 | 14 | 252 | Clear, viscous, |

TABLE 1-continued

Oligohydroxycarboxylic acids with hydroxyl end groups from glycolic acid and ethylene glycol

| Example | Adducts glycolic acid mole | Adducts ethylene glycol mole | Reaction water, % of theory | Acid Number | Calculated molecular weight g/mole | Appearance |
|---|---|---|---|---|---|---|
| 2 | 4 | 1 | >90 | 20 | 294 | light yellow Viscous, white |
| 3 | 6 | 1 | >98 | 24 | 410 | Wax-like, white |

(b) Obtained from Lactic Acid Ethyl Ester and Ethylene Glycol

In a three-necked flask equipped with stirrer and reflux condenser, ethyl lactate and ethylene glycol are combined. As catalyst, 70 ml of 0.2% methanolic sodium methylate solution are added and the make-up is subsequently heated to 150° C. The temperature is carefully increased to 180° C., and at about 80° C. ethanol constantly distills off. After sixteen hours the ethanol separation is completed and at 150° C. bath temperature evacuation at 10 Torr is carried out. The remaining material is decanted under nitrogen. The composition of the make-up and the oligomeric properties of the products are given in Table 2 (Examples 4–6).

TABLE 2

Acid Number: 296
OH-Number: <3

(b) Preparation from glycolic acid and adipic acid

In a three-necked flask equipped with stirrer and reflux condenser the dicarboxylic acid and the hydroxycarboxylic acid are introduced. The mixture is heated rapidly under nitrogen to 150° C. and then over the course of 6 hours from 150° to 200° C. Most of the reaction water thereby separates, which indicates the reaction of the ester condensation. The make-up is cooled to about 150° C., evacuated carefully at 10 Torr, and the reaction is completed at 200° C. and 10 Torr. The product is decanted while hot under nitrogen. The composition of the make-up and the properties of the oligomers are given in Table 3 (Examples 8 through 10).

TABLE 3

Oligohydroxycarboxylic acids with carboxyl end groups from glycolic acid and adipic acid

| Example | Adduct glycolic acid mole | Adduct adipic acid mole | Product yield of reaction water, % | Product acid number | Product molecular weight from the acid number g mole$^{-1}$ | Appearance |
|---|---|---|---|---|---|---|
| 8 | 1 | 1 | >99 | 620 | 181 | wax-like, solid |
| 9 | 3 | 1 | >98 | 376 | 298 | wax-like, soft |
| 10 | 4 | 1 | >96 | 334 | 336 | wax-like, soft |

Oligohydroxycarboxylic acids with hydroxy end groups from ethyl lactate and ethylene glycol

| Example | Adducts Ethyl lactate mole | Adducts Ethylene glycol mole | Product Yield of Ethanol % | Product Molecular Weight | Appearance |
|---|---|---|---|---|---|
| 4 | 2 | 1 | 95 | 193 (osmosis) | Clear, viscous, orange colored |
| 5 | 4 | 1 | 92 | — | Clear, viscous, brown |
| 6 | 6 | 1 | 96 | — | Clear, viscous, reddish brown |

Examples 7 through 10

Oligohydroxycarboxylic acids with carboxyl end groups

General Instructions (a) Through reaction of oligohydroxycarboxylic acids with hydroxyl terminal groups with succinic anhydride.

Example 7

206.3 g of the oligomer of Example 4, 200 g of succinic anhydride and 1 g of benzyltrimethylammonium methoxide (40% in methanol) are combined in a three-necked flask equipped with stirrer, reflux condenser, and nitrogen introduction, and stirred for 8 hours at 80° C. under nitrogen. The product is characterized through the following numbers:

Examples 11 through 20

Oligohydroxycarboxylic acids with polymerizable end groups (a) Oligohydroxycarboxylic acids with polymerizable end groups from oligohydroxycarboxylic acids with terminal hydroxyl groups.

In a three-necked flask equipped with stirrer and water separator, the oligohydroxycarboxylic acids with hydroxyl end groups and 1.1 equivalents of methacrylic acid per hydroxyl group are introduced. Simultaneously—in relation to the methacrylic acid—equal parts by weight of toluene and 2 wt. % each of p-toluenesulfonic acid and hydroquinone are added.

The mixture is heated to boiling with rapid stirring and the reaction water formed is removed by the water separator.

If after five hours reaction time less than 90 to 95 percent by weight of the theoretical quantity of the expected reaction water has separated, then an additional 20 percent of the initially added quantity of methacrylic acid with 2 wt. % each of paratoluenesulfonic acid and hydroquinone are added and the reaction continued.

The reaction is terminated after about 90 to 95% of the expected reaction water has formed. After cooling of the reaction product there is added twice its volume of ethanol and filtered. The clear ethanolic solution is condensed using a rotation evaporator to ¼ of the original volume, poured into a like quantity of water, and neutralized with sodium bicarbonate. The organic phase is separated, the aqueous phase shaken with toluene, the organic phases combined, washed three times with water, and dried over sodium sulfate. The solvent is removed at room temperature in a rotation evaporator at $10^{-4}$ Torr. The composition of the make-up and the properties of the polymerizable oligomers are given in Table 4 (Examples 11 through 16).

TABLE 4

| Oligohydroxycarboxylic acids with polymerizable end groups | | | |
|---|---|---|---|
| Example | Adduct diol from Example | Yield of Reaction Water, % | Appearance |
| 11 | 1 | >97 | homogeneous, thin liquid, brown |
| 12 | 2 | >95 | homogeneous, thin liquid, brown |
| 13 | 3 | >95 | homogeneous, thin liquid, brown |
| 14 | 4 | >95 | homogeneous, thin liquid, brown |
| 15 | 5 | >95 | homogeneous, viscous, brown |
| 16 | 6 | >90 | homogeneous, viscous, brown |

(b) Oligohydroxycarboxylic acids with polymerizable end groups from oligohydroxycarboxylic acids with terminal carboxyl groups In a three-necked flask equipped with stirrer and reflux condenser the oligohydroxycarboxylic acids with terminal carboxyl groups are introduced and 1.0 equivalent of glycidylmethacrylate with 0.1 percent by weight of benzyltrimethylammonium methoxide and 0.06 per cent by weight of hydroquinone are added. Under stirring, the mixture is heated during the course of 45 minutes to 80° C., and the reaction continued at 80° C. until the acid number has dropped to under 35. The reaction is normally completed after 10 to 20 hours.

The composition of the make-up and the properties of the polymerized oligomers are given in Table 5 (Examples 17 through 20).

TABLE 5

| Oligohydroxycarboxylic acids with polymerizable end groups | | | |
|---|---|---|---|
| | Adduct Dicarboxylic | Product | |
| Example | acid from Example | Acid number | Appearance |
| 17 | 7 | 24 | homogeneous, viscous, yellow |
| 18 | 8 | 30 | homogeneous, viscous, light yellow |
| 19 | 9 | 34 | homogeneous, highly viscous, light yellow |
| 20 | 10 | 31 | homogeneous, highly viscous, light yellow |

INITIATOR COMPONENT B

Initiator Component B1

Into a three-necked flask equipped with stirrer and reflux condenser, 4 moles of trimethyladipic acid and 5 moles of hexamethyleneglycol are introduced. The mixture is heated rapidly under nitrogen to 150° C. and then during the course of 6 hours from 150° to 200° C. Most of the reaction water will separate, which indicates the reaction of the ester condensation. The make-up is cooled to about 150° C., carefully evacuated at 10 Torr, and the reaction completed at 200° C. and 10 Torr. The oligoester is decanted while hot. It is viscous and brown in color.

In order to liberate the residual oxygen, 100 g of the oligoester is dissolved in 100 g of freshly distilled tetrahydrofuran (THF). Following this the solvent is removed in vacuum at $10^{-4}$ Torr. Using a glovebox, 100 g of the oligoester is again added to 100 g of distilled degassed THF and in this solution, under complete exclusion of oxygen, 41 g of 9-borabicyclo[3.3.1]nonane is added. The mixture is stirred until homogeneous. Following this, heating is carried out for one hour with stirring to 60° C. The THF is removed under vacuum and the storage vessel is closed off. The removal of samples must be carried out under a protective gas and with complete exclusion of oxygen. The product is a viscous, dark brown liquid.

Initiator Component B2

5.0 g of 9-BBN are introduced into a 250 ml flask with complete exclusion of oxygen. In this flask under a high vacuum ($10^{-4}$ Torr) 100 g of dry, freshly distilled methylmethacrylate is condensed. The flask is closed off and shaken until the 9-BBN has gone into solution. After two days the mixture shows a remarkably higher viscosity. Then, under complete exclusion of oxygen, 0.5 g of oxygen-free methacrylic acid which was distilled under argon and 5.0 g of 9-BBN are added. This mixture is stable during storage without further change in viscosity.

Initiator Components B3 and B4

In order to liberate residual oxygen, the fats, oils or fatty acid derivatives which are listed in Table 6 are dissolved in the same quantity of THF. Following this, the solvent is evacuated at $10^{-4}$ Torr. Using a glovebox there is added the same parts per weight of freshly distilled degassed THF and the fats, oils, or fatty acid derivatives are dissolved therein. Under complete exclusion of oxygen, the quantities of 9-borabicyclo[3.3.1-]nonane (9-BBN) set forth in Table 6 are added and the mixture is stirred until the 9-BBN has quantitatively gone into solution. Following this, heating for 1 hour at 60° C. is carried out. The THF is removed under vacuum and the storage vessel sealed off. The removal of samples must be carried out under a protective gas and in the complete absence of oxygen.

TABLE 6

| | | Preparation of Initiator Components B3–B4 | | | |
|---|---|---|---|---|---|
| No. | Oil, fat, fatty acid derivative | Iodine number | Quantity of 9-BBN/g per 100 g of substance | Degree of modification of the double bonds (calculated) | Product Properties |
| B3 | Oleic acid methyl ester | 85.8 | 41 | 100 | Homogeneous, low viscosity, yellow |
| B4 | Linseed oil | 178 | 86 | 100 | Homogeneous, viscous, |

TABLE 6-continued

Preparation of Initiator Components B3-B4

| No. | Oil, fat, fatty acid derivative | Iodine number | Quantity of 9-BBN/g per 100 g of substance | Degree of modification of the double bonds (calculated) | Product Properties |
|---|---|---|---|---|---|
| | | | | | light yellow |

(1) The conversion of the reaction was determined using the $^1$H—NMR spectrum
(—C$\underline{H}$ = C$\underline{H}$—resonance at = 5.3 ppm) and the $^{13}$C—NMR spectrum
(—C$\underline{H}$ = C$\underline{H}$—resonance at = 129.5 and 129.8 ppm)
A conversion of 70 + 5% was measured

Results

Selected monomers are each mixed with 5 percent by weight of a mixture of methacryloyloxyethylphosphate and bismethacryloyloxyethylphosphate and used as resin component (A). When gluing together bony materials under "simulated in-vivo conditions" and using the listed hardeners (B) (1 to 3 percent by weight of each), the following tensile strengths are obtained (Table 7).

TABLE 7

Summary of the measured tensile strengths/Ncm$^{-2}$

| Resin component A | Hardener component B | | | |
|---|---|---|---|---|
| | B1 (2K) | B2 (no-mix) | B3 (2K) | B4 (2K) |
| Example 12 | 430–1070 | 90–140 | — | — |
| Example 13 | 260–660 | 150–550 | — | 240–410 |
| Example 18 | 180–400 | 180–330 | 90–200 | 130–200 |

What is claimed is:

1. A method of bonding hard body tissues to each other or to a metal or to a synthetic material comprising the steps of:
(A) applying to one or both surfaces to be joined together a surgical bonding system comprising:
   (a) a polymerization initiating starter component which contains at least one organoboron compound; and
   (b) a polymerizable adhesive component which contains at least one resorbable (meth)-acrylate compound which is a (meth)-acrylic acid ester having more than one (meth)-acrylate group on a polyester oligomer chain that contains hydroxy-carboxylic acid segments; and
(B) joining together said surfaces.

2. A method in accordance with claim 1 wherein components (a) and (b) are mixed together before application.

3. A method in accordance with claim 1 wherein component (a) is applied first to at least one of the surfaces to be joined together and thereafter component (b) is applied to at least one of the surfaces to be joined together.

4. A method in accordance with claim 1 wherein the hard body tissues are bones.

5. A two-component surgical bonding system for the bonding of hard body tissues which comprises
(a) a polymerization initiating starter component which contains at least one organoboron compound; and
(b) a polymerization adhesive component which contains at least one resorbable (meth)-acrylate compound which is a (meth)-acrylic acid ester having more than one (meth) acrylate group on a polyester oligomer chain that contains hydroxycarboxylic acid segments.

6. A surgical bonding system in accordance with claim 5 wherein at least one (meth)-acrylate group in the resorbable (meth)-acrylate compound is on a terminal position of the polyester oligomer chain.

7. A surgical bonding system in accordance with claim 5 wherein the resorbable (meth)-acrylate compound contains a (meth)-acrylate group in both the $\alpha$ and the $\omega$ position of the polyester oligomer chain.

8. A surgical bonding system in accordance with claim 5 wherein each hydroxycarboxylic acid segment in the polyester oligomer chain of the resorbable (meth)-acrylate compound contains from 2 to 10 carbon atoms.

9. A surgical bonding system in accordance with claim 5 wherein each hydroxycarboxylic acid segment contains from 2 to 6 carbon atoms.

10. A surgical bonding system in accordance with claim 8 wherein the hydroxycarboxylic acid segments are formed from at least one of the following acids: glycolic acid, lactic acid, hydroxypropionic acid, hydroxybutyric acid, and hydroxybenzoic acid.

11. A surgical bonding system in accordance with claim 5 wherein the polyester oligomer chain in the resorbable (meth)-acrylate compound has a mean molecular weight in the range of about 200 to about 600.

12. A surgical bonding system in accordance with claim 11 wherein the polyester oligomer chain has a mean molecular weight in the range of about 300 to about 500.

13. A surgical bonding system in accordance with claim 5 wherein the resorbable (meth)-acrylate compound also contains at least one moiety derived from the following: a difunctional alcohol, and a difunctional carboxylic acid or a functionally reactive derivative thereof.

14. A surgical bonding system in accordance with claim 13 wherein a mixture of a monofunctional compound and a difunctional compound is employed in the formation of the (meth)-acrylate compound, and wherein the monofunctional compound is used in quantities not over 50 mole percent of said mixture said monofunctional compound being a monofunctional alcohol, a monofunctional carboxylic acid or functionally reactive derivative thereof, or a monofunctional amine.

15. A surgical bonding system in accordance with claim 14 wherein the monofunctional compound is used in quantities not over 10 mole percent of said mixture.

16. A surgical bonding system in accordance with claim 5 wherein the resorbable (meth)-acrylate compound has a viscosity at room temperature of from about 2000 to about 70,000 mPas.

17. A surgical bonding system in accordance with claim 16 wherein the viscosity at room temperature is from about 3,000 to about 50,000 mPas.

18. A surgical bonding system in accordance with claim 5 wherein the starter component (a) does not self-ignite when exposed to air yet will initiate polymerization of polymerizable adhesive component (b) at mammalian body temperatures when exposed to air.

19. A surgical bonding system in accordance with claim 18 wherein the organoboron compound in starter component (a) contains at least one substituent group selected from the group consisting of alkyl and aryl groups, and which can also optionally contain at least one B-H bond.

20. A surgical bonding system in accordance with claim 19 wherein the starter component (a) contains at least one alkyl boron compound selected from the group consisting of a trialkyl boron compound and an alkyl boron hydride compound.

21. A surgical bonding system in accordance with claim 5 wherein polymerization initiating starter component (a) contains at least one of the following:
  (i) a homogeneous mixture of an organic oligomer or polymer, and at least one organoboron compound which is activated by exposure to air and is compatible with polymerizable adhesive component (b) and is inert toward the organic oligomer or polymer;
  (ii) at least one polymeric organoboron compound which has, on a stable polymer matrix, boron hydride groups or organoboron groups, or a mixture of such groups, which are stable in the presence of oxygen; and
  (iii) at least one boronalkyl compound which contains boron hydride groups, or organoboron groups, or a combination thereof, on a fatty acid or fatty alcohol ester.

22. A surgical bonding system in accordance with claim 21 wherein in the homogeneous mixture in (i) the organic oligomer or polymer is a polymer based on a derivative of (meth)-acrylic acid.

23. A surgical bonding system in accordance with claim 22 wherein the derivative of (meth)-acrylic acid is an ester or amide thereof.

24. A two component surgical bonding system for the bonding of hard body tissues which comprises
  (a) a polymerization initiating starter component which contains at least one organoboron compound; and
  (b) a polymerization adhesive component which contains at least one resorbable (meth)-acrylate compound which is a (meth)-acrylic acid ester having a (meth)-acrylate group on a polyester oligomer chain that contains hydroxycarboxylic acid segments and which also contains a moiety derived from a monocarboxylic acid or functionally reactive derivative thereof.

25. A two component surgical bonding system in accordance with claim 24 wherein the (meth)-acrylate group is obtained by reaction of the terminal carboxy group of the polyester oligomer chain with the glycidyl ester of (meth)-acrylic acid.

* * * * *